（12）United States Patent
Choukroun et al.

(10) Patent No.: US 10,349,675 B2
(45) Date of Patent: Jul. 16, 2019

(54) SMOKING CESSATION DEVICE

(71) Applicant: SmokeWatchers SAS, Neuilly sur Seine (FR)

(72) Inventors: Benjamin Choukroun, Neuilly sur Seine (FR); Thomas Serval, Neuilly sur Seine (FR)

(73) Assignee: SMOKEWATCHERS SAS, Paris (FR)

( * ) Notice: Subject to any disclaimer, the term of this patent is extended or adjusted under 35 U.S.C. 154(b) by 117 days.

(21) Appl. No.: 15/033,066

(22) PCT Filed: Oct. 29, 2014

(86) PCT No.: PCT/EP2014/073182
§ 371 (c)(1),
(2) Date: Apr. 28, 2016

(87) PCT Pub. No.: WO2015/063126
PCT Pub. Date: May 7, 2015

(65) Prior Publication Data
US 2016/0278435 A1 Sep. 29, 2016

Related U.S. Application Data

(60) Provisional application No. 61/897,149, filed on Oct. 29, 2013.

(51) Int. Cl.
A24F 47/00 (2006.01)
G06F 19/00 (2018.01)
H05B 3/00 (2006.01)
(52) U.S. Cl.
CPC ........ A24F 47/008 (2013.01); G06F 19/3462 (2013.01); H05B 3/0014 (2013.01)

(58) Field of Classification Search
CPC .... A24F 47/008; A24F 47/002; A24F 47/004; A61M 11/00; A61M 11/042; A61M 15/06; G06F 17/00; G06F 1711/00
See application file for complete search history.

(56) References Cited

U.S. PATENT DOCUMENTS 4,947,875 A * 8/1990 Brooks ................. A24F 47/006
128/202.21
6,640,804 B2 * 11/2003 Ivri ...................... A61M 11/005
128/200.16
(Continued)

FOREIGN PATENT DOCUMENTS

CA 2928868 A1 5/2015
CN 106535673 A 3/2017
(Continued)

OTHER PUBLICATIONS

Ltd., Leaf Group. "Livestrong MyQuit Coach—Dare to Quit Smoking on the App Store." App Store, Sep. 20, 2013, itunes.apple.com/us/app/livestrong-myquit-coach-dare-to-quit-smoking/id383122255?mt=8.*
(Continued)

Primary Examiner — Seyed Masoud Malekzadeh
Assistant Examiner — Taryn Trace Willett
(74) Attorney, Agent, or Firm — Nixon Peabody LLP

(57) ABSTRACT

An electronic cigarette with a memory and ability to record the amount and duration of inhalation of nicotine vapor. The electronic cigarette may be integrated with a smart phone application or other software to record usage and provide feedback to the smoker. The application may include an algorithm for the development of a withdrawal schedule for the user to quit smoking or vaping.

20 Claims, 8 Drawing Sheets

(56) References Cited

U.S. PATENT DOCUMENTS

| | | | | |
|---|---|---|---|---|
| 6,684,880 B2* | 2/2004 | Trueba | ............... | A61M 15/0085 128/200.16 |
| 8,667,891 B2* | 3/2014 | Garcia | ................ | A47J 31/4403 426/431 |
| 9,363,860 B1* | 6/2016 | Lowchareonkul | ........................... | H05B 33/0857 |
| 9,933,790 B2* | 4/2018 | Blackley | ............. | G05D 7/0676 |
| 9,937,293 B2* | 4/2018 | Brauker | ............ | A61M 5/31525 |
| 2004/0030508 A1 | 2/2004 | Likness | | |
| 2005/0251289 A1* | 11/2005 | Bonney | ................. | A61M 15/00 700/244 |
| 2006/0120069 A1* | 6/2006 | West | ....................... | F21L 4/005 362/157 |
| 2008/0029109 A1 | 2/2008 | Hercules | | |
| 2008/0257367 A1* | 10/2008 | Paterno | ................. | A24F 47/008 131/328 |
| 2009/0109042 A1 | 4/2009 | Almiman | | |
| 2010/0080760 A1* | 4/2010 | Hyde | .................... | A61M 15/02 424/45 |
| 2011/0036346 A1* | 2/2011 | Cohen | ................. | A61M 15/0065 128/200.14 |
| 2011/0265806 A1* | 11/2011 | Alarcon | ................. | A24F 47/00 131/273 |
| 2012/0291791 A1* | 11/2012 | Pradeep | ................. | A24F 47/008 131/273 |
| 2013/0319439 A1* | 12/2013 | Gorelick | ............... | A24F 47/008 131/329 |
| 2014/0060552 A1* | 3/2014 | Cohen | ................. | A24F 47/008 131/273 |
| 2014/0107815 A1* | 4/2014 | LaMothe | ................ | A24F 15/18 700/90 |
| 2015/0047662 A1* | 2/2015 | Hopps | ................... | A24F 47/008 131/329 |
| 2016/0089508 A1* | 3/2016 | Smith | ................... | A61M 15/06 128/200.16 |
| 2016/0106936 A1* | 4/2016 | Kimmel | ................ | A24F 47/008 128/202.21 |
| 2016/0157524 A1* | 6/2016 | Bowen | .................. | A24F 47/008 128/200.14 |
| 2016/0219938 A1* | 8/2016 | Mamoun | .................. | G05B 15/02 |
| 2016/0334119 A1* | 11/2016 | Cameron | .................. | F24F 3/16 |
| 2017/0318861 A1* | 11/2017 | Thorens | ................ | A24F 47/008 |
| 2018/0098576 A1* | 4/2018 | Hedarchet | ............ | A24F 47/008 |

FOREIGN PATENT DOCUMENTS

| | | |
|---|---|---|
| EP | 2110034 A1 | 10/2009 |
| EP | 3062643 A1 | 9/2016 |
| PH | 12016500815 A1 | 6/2016 |
| WO | 2004075671 A1 | 9/2004 |
| WO | 2015/063126 A1 | 5/2015 |

OTHER PUBLICATIONS

International Search Report dated Nov. 2, 2015. International Application No. PCT/EP2014/073182.

International Written Opinion dated Nov. 2, 2015. International Application No. PCT/EP2014/073182.

Bo Li et al.: i-Function Fo Electronic Cigarette: Building Social Network by Electronic Cigarette; IEEE Computer Society; 2011 IEEE International Conferences on Internet of Things, and Cyber, Physical and Social Computing; Oct. 19, 2011; pp. 634-637.

International Preliminary Report on Patentability for PCT/EP2014/073182 dated May 3, 2016, 7 pages.

* cited by examiner

SMOKING CESSATION DEVICE

CROSS REFERENCE TO RELATED APPLICATIONS

The present application is a National Stage Application of International Application No. PCT/EP14/073182 entitled "SMOKING CESSATION DEVICE" filed Oct. 29, 2014, which claims priority to Provisional Application No. 61/897,149 entitled "SMOKING CESSATION DEVICE" filed Oct. 29, 2013, the contents of which are incorporated herein by reference in their entirety.

FIELD

The present disclosure relates to assistants for quitting smoking or vaping, including electronic cigarettes.

BACKGROUND

Cigarette smoke contains over 4,800 chemicals, 69 of which are linked to causing cancer. Smoking cigarettes can lower life expectancy by 13.2 years for men, and 14.5 years for women. In the United States, cigarette smoking causes over 440,000 deaths per year. According to the America Lung Association, smoking is one of the most prevalent sources of preventable death worldwide.

Quitting smoking and vaping is notoriously difficult. It is estimated that 52 percent of smokers try to quit smoking. However, 90 percent of smokers that attempt to quit smoking relapse. Many aids have been developed to quit smoking that are less harmful than cigarettes. For example, nicotine patches and nicotine gum have proven helpful in quitting smoking.

Additionally, electronic cigarettes have been developed as an aid to quit smoking by providing a less harmful source of inhaled nicotine. Instead of burning nicotine and other chemicals like convention cigarettes, electronic cigarettes vaporize a mixture of nicotine and volatile chemicals. This nicotine rich vapor may be inhaled from the cigarette. The vapor does not contain many of the harmful carcinogens that are contained in cigarettes.

However, despite these aids the failure rate of smokers trying to quit smoking is remarkably high, while the death toll is ever increasing. Thus, a profound need exists to implement an improved method to help smokers quit smoking.

OBJECTS

It is an object of the disclosure to reduce the relapse rate of smokers attempting to quit smoking or vaping.

It is an object of the present invention to improve the likelihood of quitting smoking or vaping through feedback to a user.

It is an object of the present invention to increase the support network for smokers to assist them in quitting smoking or vaping.

It is an object of the present invention to use clinical data to determine optimal weighted nicotine withdrawal schedules.

It is an object of the disclosure to reduce health care spending through reduced healthcare costs.

SUMMARY

The likelihood a smoker's attempt to quit smoking will be successful is greatly increased when the psychological aspects of smoking are addressed. Nicotine is a physically addictive drug and is associated with many social activities, which increase the difficulty of quitting smoking. In fact, studies have shown that while counseling or medication alone increases the chances of quitting smoking, the combination is more effective. For instance, nicotine replacement products can help relieve withdrawal systems when people are quitting smoking. Additionally, individual and group counseling may also increase the likelihood an attempt to quit smoking will be successful, as it addresses the psychological and behavioral addiction to smoking.

Unfortunately, the physiological and psychological aids to quit smoking are generally always separate. Therefore, many smokers attempt to quit smoking or vaping using one or the other. Additionally, the lack of integration between the physiological and psychological aids also reduces the effectiveness of an attempt to quit smoking. This is because, for example, the psychological reinforcement and support is not directly linked to the amount or actual status of the current usage of a smoker. Rather a smoker may discuss his subjective view of his success with the group, leading to dilution of social reinforcement mechanisms. Therefore, integration of the withdrawal and the group support aspects of quitting smoking would likely increase the success of an attempt to quit smoking.

Furthermore, only some data and studies exist regarding the attributes of people that try to quit smoking and the precise withdrawal schedule that would be successful for each person. Therefore, the ability to record the withdrawal schedule that resulted in successes and failures based on a broad base of data would increase the efficacy the development of a withdrawal schedule that would be effective for a given individual.

To address these difficulties and others, systems and methods have been developed to electronically manage a smoker's attempt to quit smoking. This may include an electronic cigarette with a memory and ability to record the amount and/or duration of inhalation of nicotine vapor. Additionally, the electronic cigarette may be integrated with a smart phone application or other software to record usage and provide feedback to the smoker. The application may include an algorithm for the development of a withdrawal schedule for the user to quit smoking.

In some examples, an electronic cigarette may include a microprocessor, a Bluetooth link, a battery, a vaporization system, an LED, a button, and a memory. The cigarette may include certain software or firmware linked to the microprocessor for executing the logic of the system. The microprocessor may monitor and record the number of puffs of a cigarette, the duration of each puff, the total inhaled time, the amount of nicotine ingested, the flow rate, and other aspects. The microprocessor may store the information locally, and/or send the information over the Bluetooth link to be stored externally.

The process for quitting smoking or vaping may include an application that presents the smoker with a questionnaire relating to the smoker's characteristics including height, weight, age, sex, smoking history, and other characteristics deemed relevant to quitting. The smoker may then select witnesses that provide social support and feedback during the quitting process. The application may then determine an optimal withdrawal schedule based on the smoker's individual characteristics and current usage.

Additionally, the application may be integrated with a cloud based server that aggregates data using neural networks from many users of the application to determine optimal withdrawal schedules. Furthermore, health care insurance companies may have access or integrate with the application to provide reduction in premiums based on usage or success or determine optimal risk allocation.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

Figure 1:
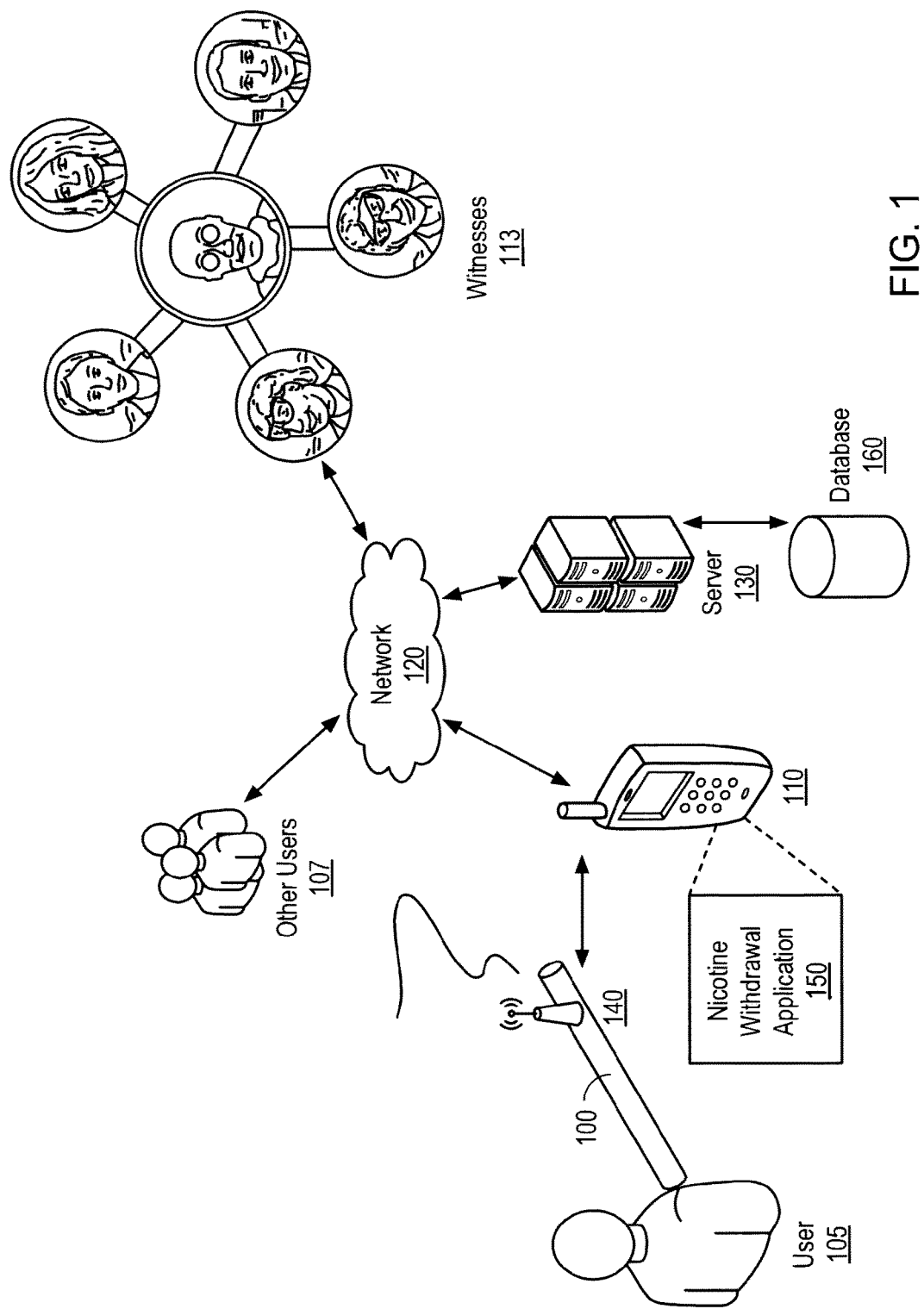
FIG. 1 is an overview of a system that implements a nicotine withdrawal program.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

In some embodiments, properties such as dimensions, shapes, relative positions, and so forth, used to describe and claim certain embodiments of the invention are to be understood as being modified by the term "about." While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

FIG. 1 illustrates the components of an embodiment of a nicotine withdrawal system in accordance with the present disclosure. The system includes an electronic cigarette 100 that may be capable of sensing the number and duration of puffs taken by a user 105. The electronic cigarette 100 may then store this data. The cigarette 100 may also transmit this data through a transreceiver 140 or other electronic communication means to a computing device 110 or over a network connection to a computing device 110.

The computing device 110 may include a nicotine withdrawal application 150 that includes program modules for implementing a quit smoking program for a user 105. The nicotine withdrawal application 150 may optimize a nicotine withdrawal schedule based on the user's 105 unique personal attributes and nicotine usage history.

The nicotine withdrawal application 150 may also aggregate input from other users 107 to optimize the nicotine withdrawal programs presented in the nicotine withdrawal application 150. Usage data from other users 107 may be sent over a network 120 to a server 130 and stored in a database 160. The server 130 may then analyze the aggregated usage data and based on medical input and research, determine optimal withdrawal programs based on each user's 105 unique attributes. The withdrawal program may be based on a daily or weekly goal for nicotine consumption that decreases over time. Accordingly, the application 150 will provide feedback to the users on whether their nicotine consumption is under the goal and/or on track to be under the goal. Additionally, FIG. 1 illustrates witnesses 113 that may be added to the application 150 to provide social support and feedback to encourage the user 107 to quit smoking or vaping. These witnesses 113 may be added form an application interface as described further herein.

Figure 2:
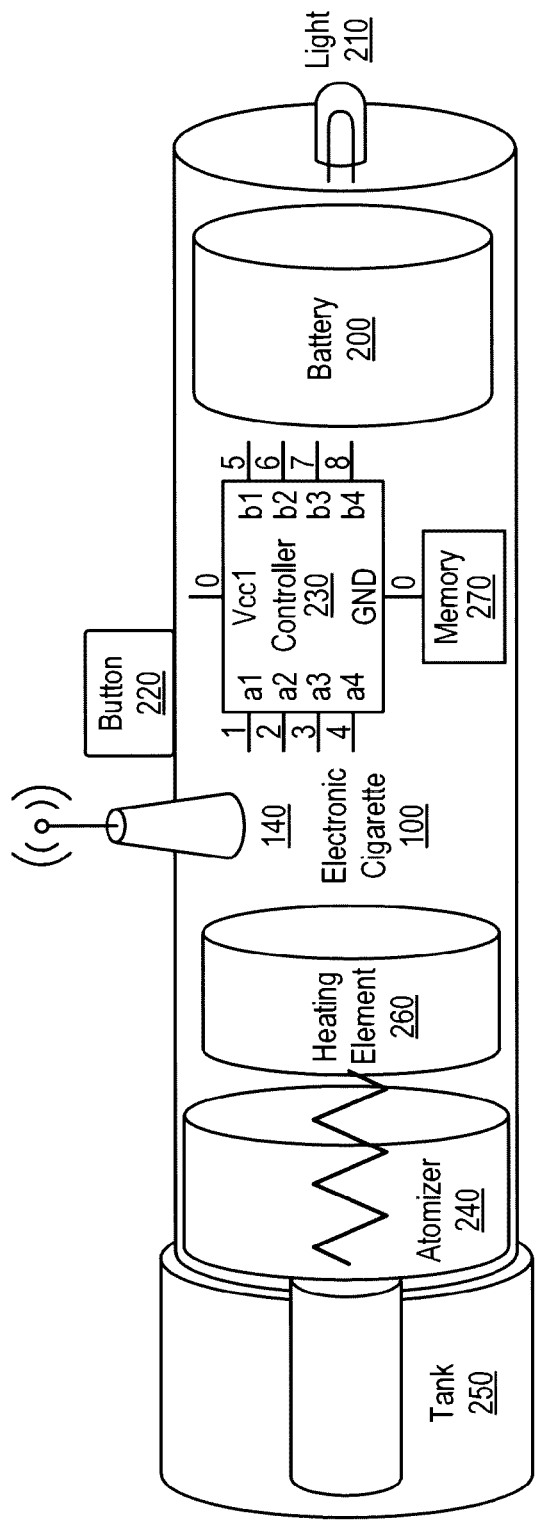
FIG. 2 is a diagram of an embodiment of the components of an electronic cigarette according to the present disclosure.

FIG. 2 illustrates a connected electronic cigarette 100 according to the present disclosure. The electronic cigarette 100 includes a button or switch 220 for actuating the cigarette 100. The button 220 may be any touch sensitive, or mechanical based button or switch. A user 105 may actuate the button 220 in order to activate the electronic cigarette 100 and inhale the nicotine rich vapor.

Actuation of the button 220 may be sensed by the controller 230 which may then send a signal to energize the heating element 260. The heating element 260 may then begin to vaporize nicotine infused liquid stored in the tank 250 inside of the atomizer 240. Once vaporized, the nicotine rich vapor may then be inhaled by the user 105 through an opening in the end of the cigarette 100. Actuation of the button 220 may also trigger a light 210 to be turned on, mimicking the lighting of a convention cigarette. This represents a single embodiment of a conventional electronic cigarette, but is not intended to be limiting. Accordingly, an electronic cigarette 100 of the present disclosure may function in any other manner using convention electronics as understood by one of skill in the art. For instance, the atomizer 240 may be replaced by other means of vaporizing the nicotine liquid. Additionally, the heating element 260 may be replaced by any other component capable of vaporizing the nicotine liquid for inhalation by a user 105. Additionally a flow sensor may trigger the heating element that indicates a user has begun inhaling in some embodiments.

The cigarette 100 may also record the duration and number of actuations of button 220 in order to determine the amount of nicotine inhaled by a user 105. Specifically, during actuation of the button 220, a controller 230 may record that the button 200 was actuated and may also record the duration of actuation. The actuation data may then be stored in the memory 270 and/or sent over a transreceiver 140 to a network, server, smartphone, or other computing device 110. A controller 230 may be any suitable controller, including a microprocessor, microcontroller, a combination of analog processing components, or other computing device(s).

The transreceiver 140 may be any device capable of wirelessly transmitting or receiving data over any number of wireless communication modes including Bluetooth, Wi-Fi, or others. The memory 270 may be any combination of volatile and non-volatile memory including RAM, ROM, cache, hard drive, or other types of memory. The memory 270 may be integrated with the controller 230 and/or a transreceiver 140 or may be separate. Additionally, the cigarette may include any suitable battery 200 to power the electronic cigarette, and other appropriate electronics and circuitry. In another embodiment, the cigarette 100 may not include a transreceiver 140 and instead may have a data connection. For instance, the cigarette 100 may include a serial or USB connection to allow a computing device 110 to download data from the memory 270.

The electronic cigarette 100 may include instructions or software stored on a computer readable medium that is readable by the controller 230 or other control system. The software may be firmware, software or other types of instructions. The software may be stored on the electronic cigarette, or may run on an applet executing remotely on a server over the network or on a wirelessly linked device, for example a smartphone or computing device 110. The software modules may be stored in the memory 270. The electronic cigarette 100 may include one or more ports for downloading new software or instructions. Additionally, new software may be transferred wirelessly over the transreceiver 140.

Figure 3:
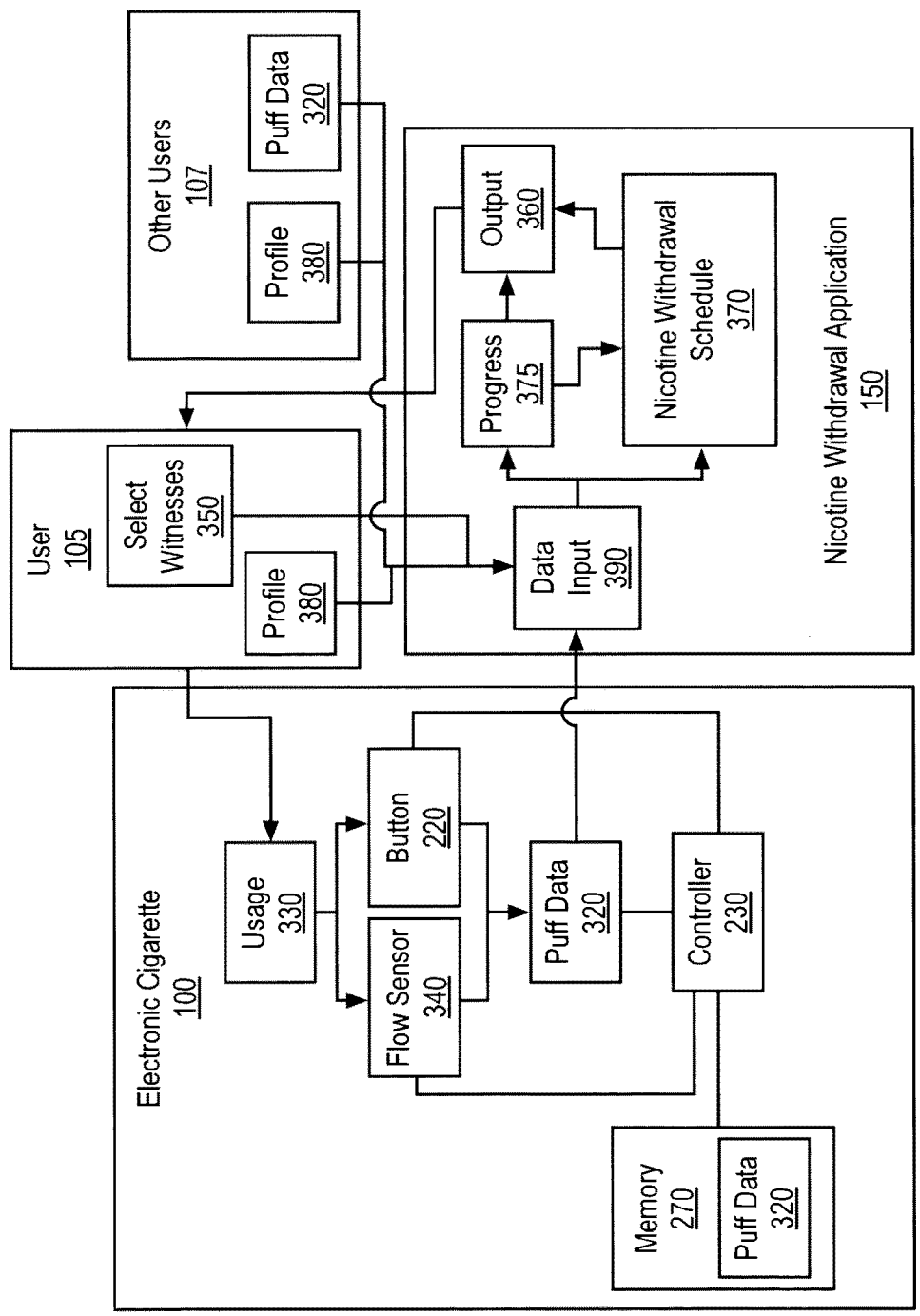
FIG. 3 is a diagram of an embodiment of a system for developing and implementing a nicotine withdrawn program.

FIG. 3 illustrates a diagram demonstrating an embodiment of the data flow logic of a nicotine withdrawal system in accordance with the present disclosure. A new user 105 seeking to quit smoking may sign up for a nicotine withdrawal application 150. Upon signing up, the user 105 may be prompted to enter their profile 380 in to the nicotine withdrawal application 150. The profile 380 includes characteristics that are relevant to nicotine withdrawal. This may include age, sex, height, weight, smoking history, including the number of cigarettes per day, the time of day of usage, and any other relevant characteristics. For example, the application 150 may request the number of cigarettes smoked per day, the brand of cigarettes, whether the user 105 smokes e-cigarettes. If the user 105 indicates through the interface that they smoke e-cigarettes, the application 150 may additionally request the user provide how long each cartridge is used and the amount of nicotine per cartridge.

Additionally, the user 105 may be prompted by the application 150 to select witnesses 350 that will provide social support through the quitting process. The nicotine withdrawal application 150 may also provide interaction or other means for witnesses to interact and support the user 105. The application 150 may allow the user 105 to post thoughts or feelings on social media sites by direct integration, or within the application 150. For example, the user 105 may be prompted to enter their current feelings, which may include that they are feeling stressed or that they are bored, and they are contemplating smoking a cigarette.

Once the initial data has been entered, the application 150 may determine an optimal nicotine withdrawal schedule 370 based on the user's 105 individual profile 380. That schedule may then be output 360 to the user 105. The output 360 may be in the form of a chart or table or other indication of the amount of cigarettes or puffs recommended for a user 105 for a particular period of time. This may include the number of cigarettes recommended for the day, week, or month, with options to display different time periods. Additionally, the user 105 may be given different options to select the pace of withdrawal from different recommended paces, some being a much faster drop from nicotine use. The output 360 may be displayed on the screen of a computing device 110 or through audio indications from the computing device 110.

In other embodiments, the user may set a daily, weekly, or monthly target nicotine consumption (e.g., in cigarettes, vapes puffs, nicotine, or other amounts) though the application 150. In those embodiments, the user's nicotine use will be compared to the daily target consumption, and provide feedback to encourage the user to smoke less or vape less than the daily target or goal set. In some embodiments, the daily target or goal will be a part of the nicotine withdrawal schedule 370, and a user can set new targets periodically as it becomes easier to hit the target. In some embodiments, the goal or will be not to smoke for a certain number of days, or not to vape for a certain number of days or a month.

In other embodiments, the withdrawal schedule 370 will utilized the same amount of puffs or or vapes on an e-cigarette but instead lower the strength of the e-liquid periodically, so the user effectively consumes less nicotine. In these embodiments, the application 150 may let the user know when they are running low to purchase a lower strength e-liquid.

In some embodiments, the user can choose the type of feedback that they prefer, including harsh, moderate or laid back. For example, an application 150 may ask the user if they want an authoritarian type coach (e.g., drill sergeant) a moderate type coach (e.g. teacher, etc.) or a laid back coach (e.g., hippie). That way, a user may customize the feedback they receive to be optimal for their motivational needs. Accordingly, if a user chooses a more authoritarian type feedback, they may receive harsher messages or more intense audio or visual warnings if they go over their goal amount for the day or are approaching it. Similarly, they may receive greater positive reinforcement for meeting their goal with certain types of feedback settings.

After a user 105 has received the output 360 including a recommended withdrawal schedule 370, the user 105 may then implement the program by taking the appropriate number of puffs from the electronic cigarette 100. The usage 330 will be recorded through actuation of the button 220 as discussed with respect to FIG. 2.

Additionally, usage 330 such as puff data 320 may be recorded based on the activation of a flow sensor 340 included in electronic cigarette 100. The controller 230 may determine whether data from the flow sensor 340 indicates a drag has been taken or determine the flow rate. Based on the flow rate and duration of actuation or inhalation, the controller 230 may determine a more accurate estimate of the amount of nicotine inhaled by a user 105. This may be performed through an algorithm including, for example, integration of the flow rate over time for the entire inhalation period. Additionally, in some embodiments, the flow rate may be determined at set time intervals while the flow rate is still above a certain threshold that is indicative of inhalation by a user 105. The flow rate for each time block may then be used to determine an amount of nicotine for each block, and those blocks may be added up over the duration of an inhalation to calculate total nicotine inhaled.

Additionally, the controller 230 may utilize data from a flow sensor 340 to ensure that inadvertent activation of the button 220 is not recorded as puff data 320. This may eliminate the system from registering false positives. The controller 230 may only record a puff data 320 when activation of the button 220 is accompanied by a sufficient rate and/or duration of airflow recorded by the flow sensor 340.

In other embodiments, actuation of the button 220 for more than a predefined amount of time will indicate usage. This will additionally help eliminate false positives.

Once puff data 320 has been recorded, the controller 230 may route the data to be saved in a memory 270 of the electronic cigarette 100 or be routed to be input 390 to the nicotine withdrawal application 150 or both. The application 150 may then process the puff data 320 to determine progress 375 of the user 105 with respect to the nicotine withdrawal schedule 370 determined by the application 150. In some embodiments, this may be performed on a control system that integrated with the electronic cigarette 100. In other embodiments, this will be performed on a computing device running the application 150. The progress 375 may then be output 360 to the user 105 by an indication on the electronic cigarette 100 or an output to a display on the computing device 110. The output 360 of the progress 375 may include the puff data 320 presented in different forms on a display of a computing device 110, or it may include a comparison of the puff data 320 to the goals encompassed in the withdrawal schedule 370. In some embodiments, this may include a color coded indication of the progress (e.g., red means nicotine use has exceeded that allotted by goal).

Additionally, puff data 320 input 390 into the application 150 may be utilized to modify the nicotine withdrawal schedule 370. The modifications may be based on puff data 230, progress 375, and/or feedback from the user 105 into the application 150. The modified withdrawal schedule 370 may then be output 360 back to the user 105.

Additionally, a purveyor of a nicotine withdrawal application 150 may partner with a liquid nicotine provider. Accordingly, a progress 375 output may be used to determine the price of refills for the tank 250. If the user 105 is making substantially good progress 375, the provider may lower the price of a refill. This will provide an additional economic incentive for the user 105 to quit smoking.

Health insurance providers may also have networks that interface with a nicotine withdrawal application 150. Accordingly, the health care providers may monitor progress 270 data from users 105 and may provide discounts on premiums depending on the success or failure based on the progress 270. Additionally, health insurance providers may be able to calculate risk pools based on puff data 320 and progress 375 data from user 105 and other users 107.

A nicotine withdrawal schedule 370 for a particular user 105 may be optimized through analysis of data from other users 107. The profile 380 data and puff data 320 from other users 107, including their progress 375, may also be input 390 into the application 150. The application 150 may then utilize that data, and compare it to the user's 105 profile 380, puff data 390, and/or progress 375, and determine an optimal nicotine withdrawal schedule 370. For example, users 105 that have similar characteristics may benefit from utilizing a similar withdrawal schedule 370. Additional, the third party usage progress 375 data will determine the success rate of other users 107 with respect to a particular nicotine withdrawal schedule 370. Accordingly, this can be utilized to predict the success of a particular withdrawal schedule 370 of a unique user 105 based on their profile 380 and/or puff data 320.

For example, a study published in BioMed Central titled Effect of an Electronic Nicotine Delivery Device (e-Cigarette) on smoking reduction and cessation: a prospective 6-month pilot, studied the success rate of e-cigarettes on reducing cigarette smoking. The study grouped participants with similar characteristics including participants smoking at least 15 factory cigarettes per day for at least the past 10 years who did not want to quit smoking. The allowed the participants to smoke up to 4 cartridges of e-cigarettes per day. The study showed a significant decrease in the number of factory cigarettes smoked for each participant from 25 to 5 per day at week 24.

Accordingly, an application 150 in accordance with the present disclosure may group users 105 with profile 380 data similar to the above study and implement a similar reduction program. However, this represents just one mode of reducing smoking. After additional puff data 320 and progress data 375 is analyzed, more specific grouping and effective smoking cessation programs may be developed.

After analysis of large pools of progress 375 data from other users 107, it might be determined that certain characteristic in a profile 380 would indicate the optimum selection for a particular component of a withdrawal schedule 370. For example, it may be determined that users 105 who are a certain age or weight, may be able to be more successful or achieve better progress 375 from a schedule that has a higher rate of decrease of nicotine usage per week, or month. As another example, specific amounts of prior smoking may require a different rate of withdrawal. Other factors of the withdrawal may be varied in addition to the rate, including potential timing of step downs, the timing of nicotine use throughout the day, and the spacing of nicotine use throughout the day (i.e., many shorter puffs or fewer longer puffs). Additionally, the process of analyzing data from other users 107 may be facilitated through a neural network.

Figure 4:
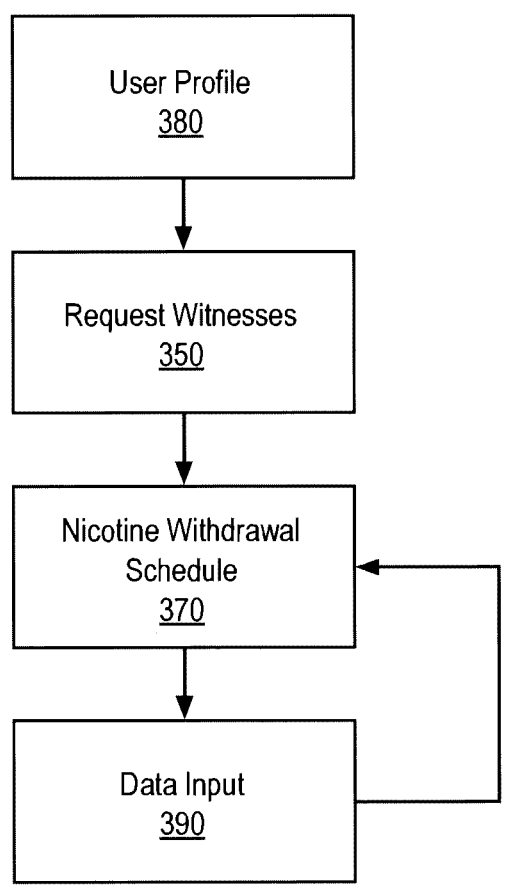
FIG. 4 illustrates a step-by-step process for implementing a program to assist a user in a scheduled withdrawal from nicotine according to the present disclosure.

FIG. 4 illustrates an embodiment of a process that may be utilized by an application 150 for implementing a withdrawal program 410. First, the application 150 may request a user profile 380. Next, the application may request witnesses 350 to provide social support during the process of quitting smoking. Then the application 150 may determine an optimal nicotine withdrawal schedule 370. Additionally, usage may trigger data input 390 from which the nicotine withdrawal schedule 370 which may be appropriately modified.

In some embodiments, when a user is experiencing a craving, the application 150 may have an interface 510 input that allows to alert witnesses 350 to a craving. This will provide a method of immediate social support to get through a craving. In some embodiments, the coach or motivational person may also provide feedback when a user indicates they are having a craving. This may be in the form of messages from the coach through the application 150 interface 510.

Figure 5:
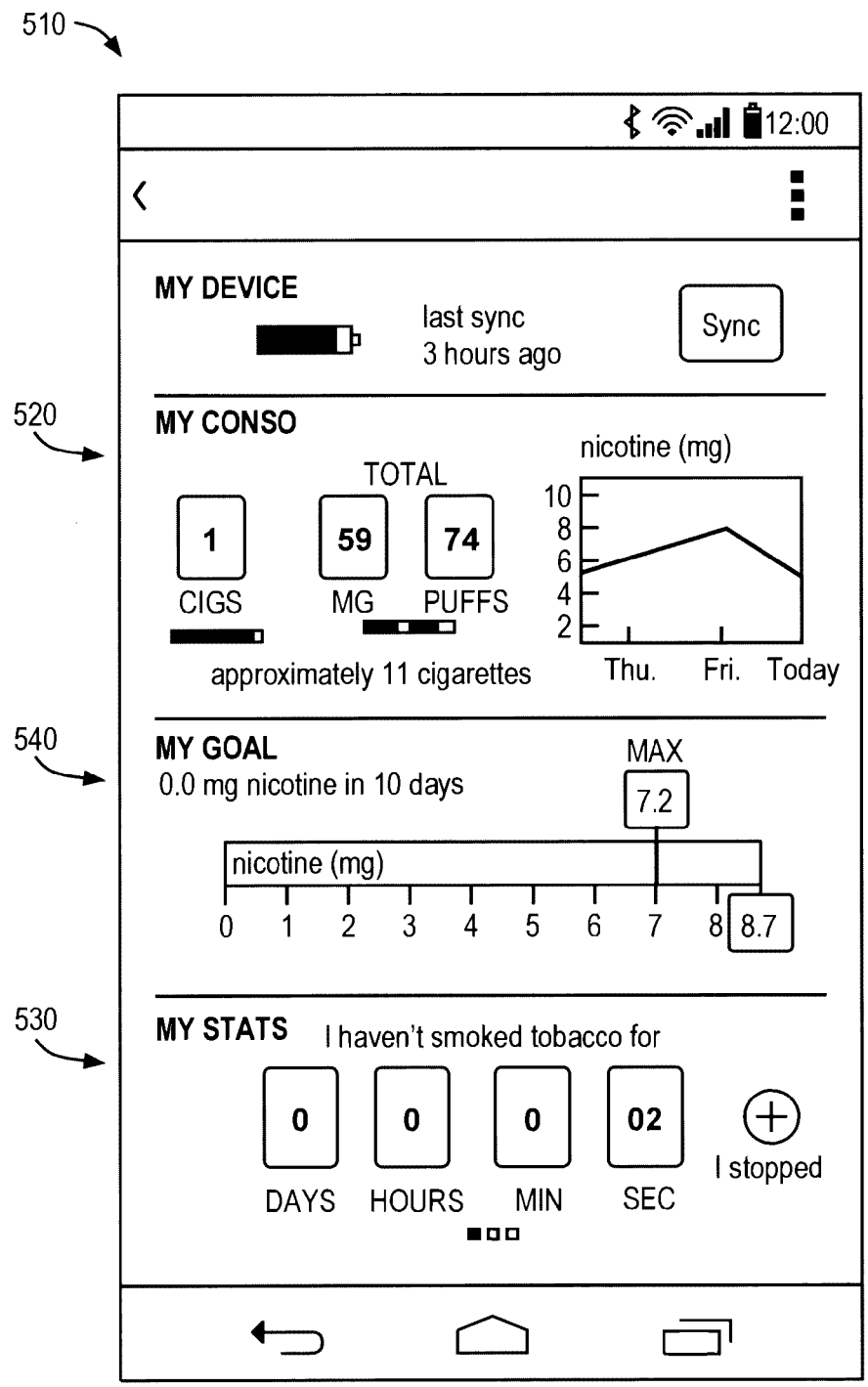
FIG. 5 illustrates an embodiment of a user interface according to the present disclosure.
Figure 6:
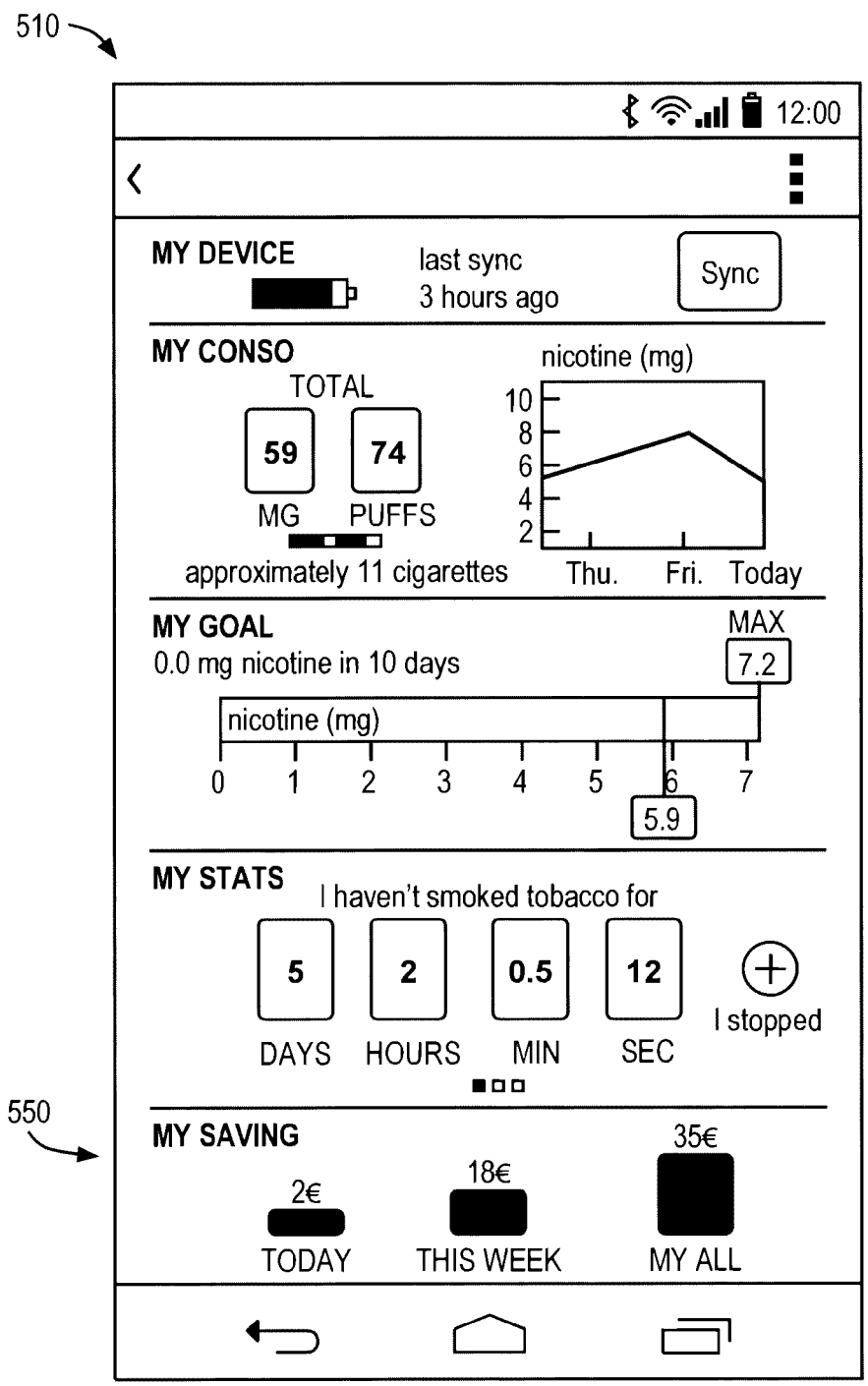
FIG. 6 illustrates an embodiment of a user interface according to the present disclosure.

FIGS. 5 and 6 include example interfaces 510 that the nicotine withdrawal application 150 may present to the user 105 on a mobile device or other computing device 110. One of the major hurdles to quitting smoking is the positive reinforcement experienced immediately after smoking a cigarette and the delayed negative or uncertain reinforcement as a consequence. Users 105 may not develop lung cancer or other adverse conditions for years after smoking, and the effect or adverse consequences of each individual cigarette are largely uncertain and unknown. Indeed, psychological research has demonstrated that punishment or adverse consequences are more effective motivators when administered immediately after the target behavior than when it is delayed. For example, Alan Kazdin's Behavior Modification in Applied Settings: Seventh Edition, quotes several studies relating to delay of punishment. The studies demonstrate that even brief delays can reduce the effectiveness of punishment. Additionally, adverse feedback or consequences are more effective when the consequences occur every time the behavior occurs.

Accordingly, the present disclosure provides a method of providing near immediate and continual feedback to the user 105 in order to provide further motivation to quit smoking. The feedback is provided through the application 150 by way of the user interface 510. FIGS. 5 and 6 demonstrate examples of types of feedback that may be provided to a user 105. These include, for example, a usage indicator 520. A usage indicator 520 may display indications of the number of cigarettes smoked, potentially in a red or negative color depending on the progress 375 toward the user's goal or withdrawal schedule 370, the amount of nicotine consumed from the electronic cigarette, for example in mg, or puffs, and a chart showing the nicotine usage statistics selectable for different time periods, including days, weeks, months, and years or other timeframes. The usage indicator may display this information in quantitative or numerical format, or display it in qualitative formats such as bar graphs and color coded usage indicators. In some embodiments, the user may vary the amount of nicotine vaporized by manipulating the voltage control. In some embodiments, the voltage may be increased or decreased by scrolling left or right on the keyboard. This may be implemented by an application interface that allows voltage increase or decrease by a throttle, arrows, joystick, or other representation of a throttle control that will vary the amount of nicotine breathed in for an average puff. In some embodiments, scrolling left less than is will increase the voltage 0.1 and scrolling right will decrease the voltage 0.1.

The feedback to user may also include an abstinence timer 530 indicating the amount of time since the last cigarette has smoked, and an option to indicate the user 105 "slipped" and has smoked a cigarette. In some embodiments, and as shown in FIG. 6, the feedback through an interface 510 may also include a savings indicator 610 that displays the amount of money saved through abstaining from smoking. This may be calculated and displayed over several different time periods to increase the immediacy and quality of feedback including over the day, week and overall. The application 150 and/or computing device may calculate the amount of money saved by comparing the amount of cigarettes the user was smoking when they started the program with the amount of cigarettes smoked (or effective cigarettes based on nicotine consumption) during the withdrawal schedule 370.

Figure 7:
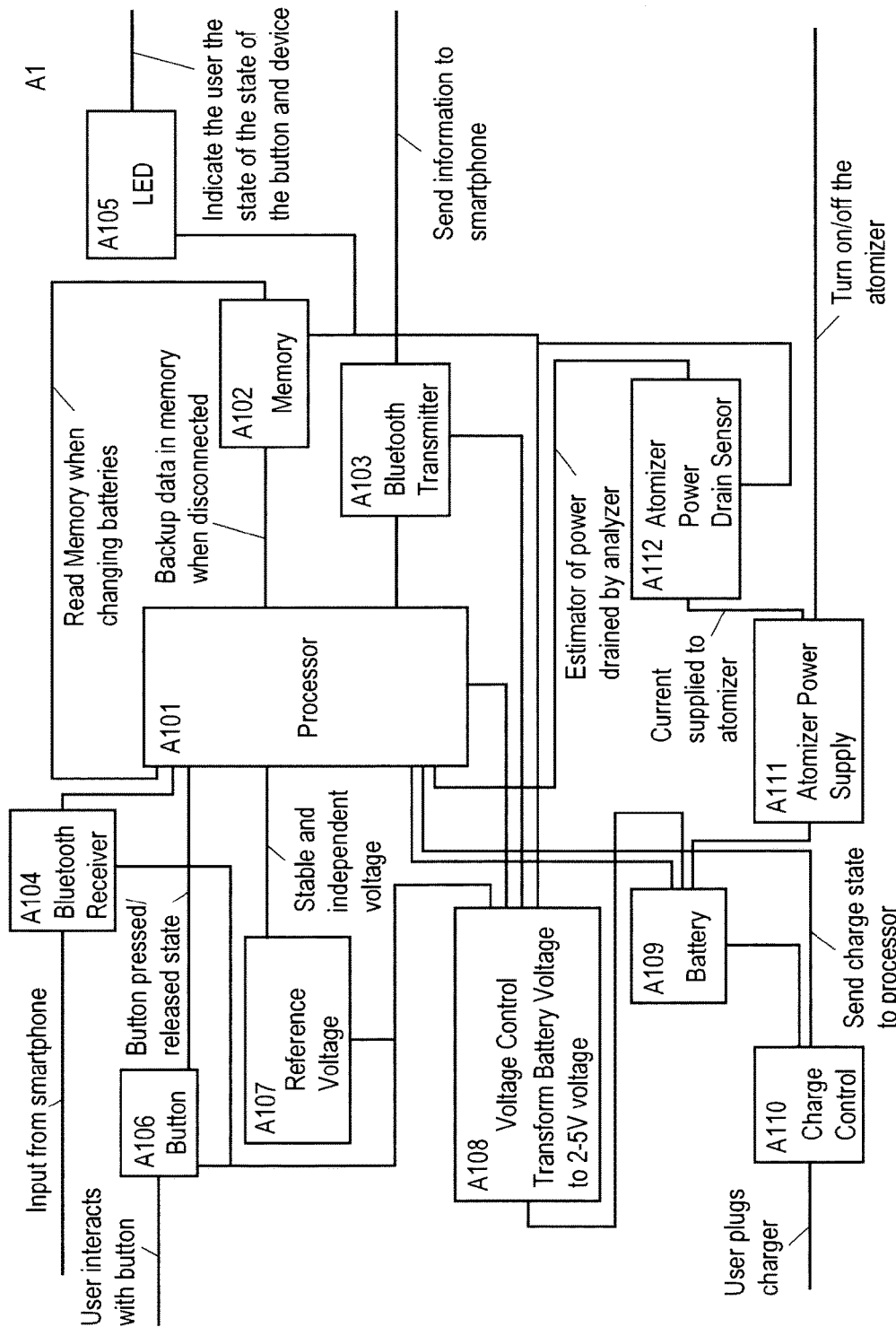
FIG. 7 illustrates an embodiment of the electrical components according to the present disclosure.

Additionally the application 150 interface 510 may include, based on the nicotine withdrawal schedule 370 and/or the progress 375, a goal progress indicator 540. The progress indicator 540 may include various indications of the user's 105 progress 375 on meeting the goals of the nicotine withdrawal schedule 370. This may include a bar graph demonstrating the weekly progress, percentage, milligrams, or other indication of how much of the week's allotted nicotine has been consumed, based on usage of the electronic cigarette 100. In some embodiments, the progress indicator 540 may include color coding indicating, for instance, in red if the user has exceeded their goal or green if they have not. In some embodiments, the progress indicator 540 may be green or yellow if the user has not reached their goal or exceeded their goal number of puffs, mg, cigarettes or other measure of smoking. In some embodiments, it will be blue if a user is on track, or white if there is no goal in process. This goal progress indicator 540 may be provided through the user interface 510, or in some embodiments, may be provided on the light 210 as shown in FIG. 7 as indicating the state of the device. The goal may be a target cigarettes or nicotine per day, week, or month. In some embodiments, the goal will be a weekly or daily consumption amount that will decrease overtime in accordance with a withdrawal schedule 370.

In some embodiments, the application may include "my smokers" that displays their puffs/day or cigs/day. In some embodiments, the interface 510 may include a joystick or other functionality for varying voltage supplied to the electronic cigarette 100.

FIG. 7 illustrates an example of a circuit diagram of the electronic components of an electronic cigarette 100. The electronic components include a processor or controller 230, a transreceiver 140, or a transmitter and a receiver separate from each other, an LED or other light 210, memory 270, battery, 200, charge control, atomizer power supply, voltage control, reference voltage, button, and other components as indicated. Accordingly this only provides an example of the electronic components, and other configurations and components may be implemented in order to provide a connected electronic cigarette 100. The status of the device as indicated by A105, for example may be communicated by the LED light 210 in different colors or flashing patterns that represent for example, charging, vaping, synching, low battery, or other statuses.

Figure 8:
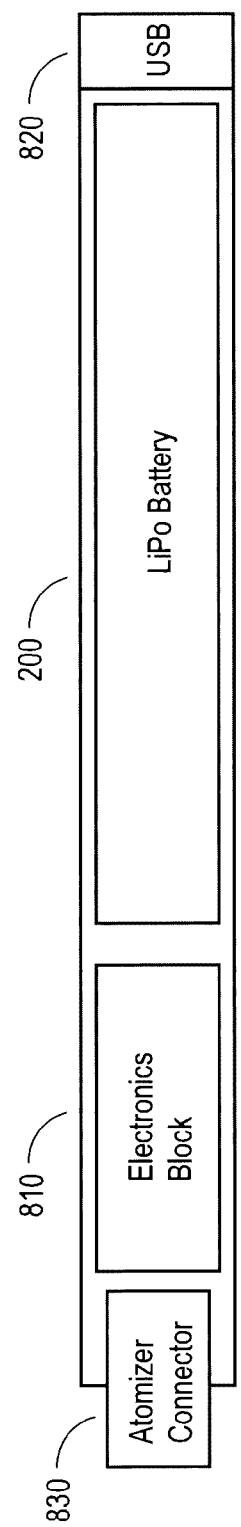
FIG. 8 illustrates an embodiment of the components of a connected electronic cigarette according to the present disclosure.

FIG. 8 illustrates a schematic diagram of an example of the internal components of an electronic cigarette 100 according to the present disclosure. The cigarette 100 includes a battery 200, data interface 820, such as a USB port, and an atomizer connector 830. The connector 830 includes the ability to connect to the refill cartridge containing an atomizer 240 and a tank 250 filled with volatile chemicals and nicotine.

In some embodiments, the device will include a smart buzzer that includes a find me function on the mobile application 150. By pressing find me on the application 150 interface, the buzzer may sound allowing a user to find the e-cigarette.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. An electronic cigarette for assisting in a smoking or vaping cessation program comprising:
   a controller;
   a memory in electrical communication with the controller;
   a vaporizing chamber;
   a heating element integrated with the vaporizing chamber;
   a storage tank in fluid communication with the vaporizing chamber;

a button in electrical communication with the controller, the button being configured to actuate the controller to cause the heating element to vaporize at least a portion of a substance in the storage tank such that vapor enters into the vaporizing chamber and is ready for consumption by a user of the electronic cigarette; and a flow rate sensor in electrical communication with the controller, wherein the controller is configured to determine, using the flow rate sensor, if a flow of the vapor from the vaporizing chamber exceeds a flow rate threshold and exceeds a duration threshold that is indicative of inhalation by the user of at least a portion of the vapor, and wherein the controller is configured to only record actuation data representing at least one actuation of the button when the actuation of the button is accompanied by the flow of the vapor exceeding both the flow rate threshold and the duration threshold, such that inadvertent activation of the button is not recorded as actuation data.

2. The electronic cigarette of claim 1 wherein the actuation data includes a number of actuations of the button and a duration of each actuation of the button.

3. The electronic cigarette of claim 1, wherein the controller is configured to continually record the actuation of the button for an entire duration of the actuation of the button.

4. The electronic cigarette of claim 1, wherein a transceiver is in electrical communication with the controller and is configured to transmit actuation data.

5. A method for determining a substance withdrawal schedule for a user based on a unique user profile to quit smoking or vaping, the method comprising:

receiving profile information associated with a first user of an electronic cigarette;

receiving peer progress data associated with other users of other electronic cigarettes, the peer progress data including peer profile information and peer use data;

comparing the received profile information associated with the first user to the peer profile information;

based at least in part on the comparison and the peer use data, determining a substance withdrawal schedule for the first user, the substance withdrawal schedule providing a first recommended number of consumption sessions, via the electronic cigarette, of a substance having a first strength for the first user during a first period of time;

displaying, on a display device, at least a portion of the determined substance withdrawal schedule;

determining, using a flow rate sensor of the electronic cigarette, if a flow of vapor flowing through a chamber of the electronic cigarette exceeds a flow rate threshold and exceeds a duration threshold that is indicative of inhalation by the first user of at least a portion of the vapor;

recording use data representing at least one actuation of a button of the electronic cigarette only in response to the button being activated in conjunction with the flow of the vapor exceeding both a flow rate threshold and a duration threshold, such that inadvertent activation of the button is not included in the use data;

receiving the use data from the electronic cigarette associated with the first user;

based at least in part on the received use data associated with the first user, modifying the substance withdrawal schedule, the modified substance withdrawal schedule providing a second recommended number of consumption sessions, via the electronic cigarette, of the substance having a second strength for the first user during a second period of time that is separate and distinct from the first period of time; and displaying, on the display device, at least a portion of the modified substance withdrawal schedule.

6. The method of claim 5, further comprising maintaining a database of peer progress data from other users.

7. The method of claim 5, wherein the use data includes a number of actuations of the button and a duration of each actuation of the button.

8. The method of claim 5, further comprising continuously or periodically modifying the substance withdrawal schedule based on the received use data associated with the first user.

9. The method of claim 5, wherein the first recommended number of consumption sessions and the second recommended number of consumption sessions are the same.

10. The method of claim 9, wherein the second strength of the substance is less than the first strength of the substance.

11. The method of claim 5, further comprising prompting the first user to provide a witness to provide support to the first user as needed.

12. The method of claim 11, further comprising transmitting an alert to the provided witness, the alert being associated with a craving of the first user.

13. A device for providing feedback on nicotine use, the device comprising:

a controller;
a memory in electrical communication with the controller;
a vaporizing chamber;
a heating element integrated with the vaporizing chamber;
a progress indicator that is configured to provide an indication of a user's progress towards a goal;
a storage tank in fluid communication with the vaporizing chamber;
a button in electrical communication with the controller such that activation of the button causes the controller to activate the heating element; and
a flow rate sensor in electrical communication with the controller, wherein the controller is configured to determine, using the flow rate sensor, if a flow of vapor flowing through the vaporizing chamber exceeds a flow rate threshold and exceeds a duration threshold that is indicative of inhalation by the user of at least a portion of the vapor, wherein the controller is configured to only record actuation data representing at least one actuation of the button when the actuation of the button is accompanied by the flow of vapor exceeding both the flow rate threshold and the duration threshold, such that inadvertent activation of the button is not recorded as actuation data, and wherein the controller is further configured to automatically instruct the progress indicator to display an indication of the user's progress based at least in part on the recorded actuation data.

14. The device of claim 13, wherein the progress indicator is a visual indicator.

15. The device of claim 13, wherein the progress indicator is a color coded light source.

16. The device of claim 15, wherein the controller is configured to change an illuminated color of the color coded light source based on a comparison between the recorded actuation data and a nicotine withdrawal schedule.

17. A method for providing a user with an indication of their compliance with a substance withdrawal schedule, the method comprising:
- receiving use data from an electronic cigarette, the electronic cigarette including:
  - a controller;
  - a heating element;
  - a button being configured to cause the heating element to vaporize at least a portion of a substance, thereby creating vapor; and
  - a flow rate sensor;
- determining, using the flow rate sensor, if a flow of the created vapor exceeds a flow rate threshold and exceeds a duration threshold that is indicative of inhalation by a user of at least a portion of the created vapor;
- recording actuation data associated with a button activation duration and a number of actuations of the button only in response to the button being activated in conjunction with the flow of the created vapor exceeding both the flow rate threshold and the duration threshold, such that inadvertent activation of the button is not recorded as actuation data;
- calculating an estimated amount of the substance inhaled by the user based at least in part on the recorded actuation data;
- comparing the recorded actuation data to a substance withdrawal schedule and determining a level of compliance with the substance withdrawal schedule based on the comparison; and
- outputting an indication of the determined level of compliance to the user.

18. The method of claim 17, wherein the indication of the determined level of compliance is a color output of a light source, a textual indication on a display, or both.

19. The method of claim 17, wherein the indication of the determined level of compliance is a color coded symbol on a display.

20. The method of claim 17, wherein the indication of the determined level of compliance is a bar graphical representation of the amount smoked in comparison to the substance withdrawal schedule.

* * * * *